US006242468B1

(12) United States Patent
Li et al.

(10) Patent No.: US 6,242,468 B1
(45) Date of Patent: Jun. 5, 2001

(54) CARBAMATE AND UREA COMPOSITIONS AND NEUROTROPHIC USES

(76) Inventors: Jia-He Li, 27 Manor Ct., Cockeysville, MD (US) 21030; Joseph P. Steiner, 988 Sugar Maple St., Hampstead, MD (US) 21074; Gregory S. Hamilton, 6501 Frederick Rd., Catonsville, MD (US) 21228

( * ) Notice: Subject to any disclaimer, the term of this patent is extended or adjusted under 35 U.S.C. 154(b) by 0 days.

(21) Appl. No.: 09/139,672

(22) Filed: Aug. 25, 1998

Related U.S. Application Data

(63) Continuation-in-part of application No. 08/805,646, filed on Feb. 27, 1997.

(51) Int. Cl.$^7$ .......................... A61K 31/44; A61K 31/40; A61K 31/445; A61K 31/16
(52) U.S. Cl. .......................... 514/343; 514/342; 514/423; 514/330; 514/613; 514/316; 514/317
(58) Field of Search ................................. 514/316, 317, 514/613, 330, 423, 342, 343

(56) References Cited

U.S. PATENT DOCUMENTS

| | | | |
|---|---|---|---|
| 4,985,458 | 1/1991 | Nakayama et al. | 514/533 |
| 5,102,906 | 4/1992 | Nakayama et al. | 514/452 |
| 5,166,317 | 11/1992 | Wallace et al. | 514/350 |
| 5,214,034 | 5/1993 | Nakayama et al. | 514/159 |
| 5,215,969 | 6/1993 | Springer et al. | 514/21 |
| 5,232,923 | 8/1993 | Fukazawa et al. | 514/237.5 |
| 5,620,971 | 4/1997 | Armistead et al. | 514/217.03 |
| 5,780,484 | 7/1998 | Zelle et al. | 514/316 |
| 5,935,989 | * 8/1999 | Hamilton et al. | 514/423 |

FOREIGN PATENT DOCUMENTS

| | | |
|---|---|---|
| WO 88/09789 | 12/1988 | (WO) . |
| WO 95/26337 | 10/1995 | (WO) . |
| WO 96/41609 | 12/1996 | (WO) . |
| WO 97/36869 | 10/1997 | (WO) . |
| WO 98/20891 | 5/1998 | (WO) . |
| WO 98/20892 | 5/1998 | (WO) . |
| WO 98/20893 | 5/1998 | (WO) . |

OTHER PUBLICATIONS

Dumont, Francis J. et al., "The Immunosuppressive and Toxic Effects of FK–506 are Mechanistically Related: Pharmacology of a Novel Antagonist of FK–506 and Rapamycin," *J. Exp. Med.*, 1992, 176, 751–760.

Schreiber, Stuart L., "Chemistry and Biology of the Immunophilins and Their Immunosuppressive Ligands," *Science*, 1991, 251, 282–287.

Database WPIDS on STN, Vertex Pharmaceuticals Inc., WPIDS No. 92–433329, Duffy, J.P., "New alpha–sulfonyl aminocarbonyl derivs.—have affinity for the FK–506 binding protein, are immunosuppressants for treating auto–immune disease, transplant rejection, etc.", abstract, WO–9221313 A2, Dec. 10, 1992. See entire abstract.

Snyder, Solomon H. and Sabatini, David M., "Immunophilins and the nervpous system," *Nature Medicine*, 1995 1(1), 32–37.

Gold, Bruce G. et al., "Regulation of aberrant neurofilament phosphorylation in neuronal perikarya. IV. Evidence for the involvement of two signals," *Brain Research*, 1993 626, 23–30.

Gold, Bruce G. et al., "Regulation of the trancription factor c–JUN by nerve growth factor in adult sensory neurons," *Neuroscience Lett.*, 1993 154, 129–133.

Gold, Bruce G. et al., "The immunosuppressant FK506 increases functional recovery and nerve regeneration following peripheral nerve injury," *Rest. Neur. and Neuroscience*, 1994 6, 287–296.

Gold, Bruce G. et al., "Multiple signals underlie the axotomy–induced up–regulation of c–JUN in adult sensory neurons," *Neuroscience Lett.*, 1994 176, 123–127.

Lyons, W. Ernest et al., "Immunosuppressant FK506 promotes neurite outgrowth in cultures of PC12 cells and sensory ganglia," *Proc. Natl. Acad. Sci. USA*, 1994, 91, 3191–3195.

Gold, Bruce G. et al., "The Immunosuppressant FK506 Increase the Rate of Axonal Regeneration in Rat Sciatic Nerve," *Jour. Neuroscience*, 1995 15(11), 7509–7516.

Lyons, W. Ernest et al., "Neuronal Regeneration Enhances the Expression of the Immunophilin FKBP–12", *Jour. Neuroscience*, 1995(15)4, 2985–2994.

Steiner, J.P. et al., "Nonimmunosuppressive Ligands for Neuroimmunophilins Promote Nerve Extension In Vitro and In Vivo", *Society for Neuroscience Abstracts*, 1996 22(297.13).

Dragovich, Peter S. et al., "Structure–Based Design of Novel, Urea–Containing FKBP12 Inhibitors," *J. Med. Chem.*, 1996 39, 1872–1884.

* cited by examiner

Primary Examiner—Theodore J. Criares

(57) ABSTRACT

This invention relates to pharmaceutical compositions and methods for effecting a neuronal activity using low molecular weight, small molecule carbamates and ureas having an affinity for FKBP-type immunophilins.

44 Claims, No Drawings

CARBAMATE AND UREA COMPOSITIONS AND NEUROTROPHIC USES

This application is a continuation-in-part of U.S. patent application Ser. No. 08/805,646, filed Feb. 27, 1997, pending, the entire contents of which are herein incorporated by reference.

BACKGROUND OF THE INVENTION

1. Field of Invention

This invention relates to pharmaceutical compositions and methods for effecting a neuronal activity using low molecular weight, small molecule carbamates and ureas having an affinity for FKBP-type immunophilins.

2. Description of Related Art

The term immunophilin refers to a number of proteins that serve as receptors for the principal immunosuppressant drugs, cyclosporin A (CsA), FK506 and rapamycin. Known classes of immunophilins are cyclophilins and FK506 binding proteins, or FKBPs. Cyclosporin A binds to cyclophilin A while FK506 and rapamycin bind to FKBP12. These immunophilin-drug complexes interface with various intracellular signal transduction systems, especially the immune and nervous systems.

Immunophilins are known to have peptidyl-prolyl isomerase (PPIase), or rotamase, enzyme activity. It has been determined that rotamase enzyme activity plays a role in the catalyzation of the interconversion of the cis and trans isomers of peptide and protein substrates for the immunophilin proteins.

Immunophilins were originally discovered and studied in the immune tissue. It was initially postulated by those skilled in the art that inhibition of the immunophilins' rotamase activity leads to inhibition of T-cell proliferation, thereby causing the immunosuppressive activity exhibited by immunosuppressant drugs, such as cyclosporin A, FK506 and rapamycin. Further study has shown that the inhibition of rotamase activity, in and of itself, does not result in immunosuppressive activity. Schreiber et al., *Science*, 1990, vol. 250, pp. 556–559. Instead, immunosuppression appears to stem from the formulation of a complex of immunosuppressant drug and immunophilin. It has been shown that immunophilin-drug complexes interact with ternary protein targets as their mode of action. Schreiber et al., *Cell*, 1991, vol. 66, pp. 807–815. In the case of FKBP-FK506 and cyclophilin-CsA, the immunophilin-drug complexes bind to the enzyme calcineurin and inhibit the T-cell receptor signalling which leads to T-cell proliferation. Similarly, the immunophilin-drug complex of FKBP-rapamycin interacts with the RAFT1/FRAP protein and inhibits the IL-2 receptor signalling.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release and neuronal process extension.

Surprisingly, it has been found that certain low molecular weight, small molecule carbamates and ureas with a high affinity for FKBPs exhibit excellent neurotrophic effects. Furthermore, the compounds are devoid of immunosuppressive activity. These findings suggest the use of low molecular weight, small molecule carbamates and ureas in treating various peripheral neuropathies and enhancing neuronal regrowth in the central nervous system (CNS). Studies have demonstrated that neurodegenerative disorders such as Alzheimer's disease, Parkinson's disease, and amyotrophic lateral sclerosis (ALS) may occur due to the loss, or decreased availability, of a neurotrophic substance specific for a particular population of neurons affected in the disorder.

Several neurotrophic factors affecting specific neuronal populations in the central nervous system have been identified. For example, it has been hypothesized that Alzheimer's disease results from a decrease or loss of nerve growth factor (NGF). It has thus been proposed to treat SDAT patients with exogenous nerve growth factor or other neurotrophic proteins, such as brain derived growth factor, glial derived growth factor, ciliary neurotrophic factor and neurotropin-3, to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressant drugs exhibit a number of potentially serious side effects including nephrotoxicity, such as impairment of glomerular filtration and irreversible interstitial fibrosis (Kopp et al., *J. Am. Soc. Nephrol.*, 1991, 1:162); neurological deficits, such as involuntary tremors, or non-specific cerebral angina, such as non-localized headaches (De Groen et al., *N. Engl. J. Med.*, 1987, 317:861); and vascular hypertension with complications resulting therefrom (Kahan et al., *N. Engl. J. Med.*, 1989, 321:1725).

To prevent the side effects associated with the use of the immunosuppressant compounds, the present invention provides a method of using a non-immunosuppressive compound containing low molecular weight, small molecule carbamates and ureas to enhance neurite outgrowth, and to promote neuronal growth and regeneration in various neuropathological situations where neuronal repair can be facilitated, including: peripheral nerve damage caused by physical injury or disease state such as diabetes; physical damage to the central nervous system (spinal cord and brain); brain damage associated with stroke; and neurological disorders relating to neurodegeneration, such as Parkinson's disease, SDAT (Alzheimer's disease), and amyotrophic lateral sclerosis.

SUMMARY OF THE INVENTION

The present invention relates to a method of using a neurotrophic low molecular weight, small molecule carbamates and ureas having an affinity for FKBP-type immunophilins. Once bound to these proteins, the neurotrophic compounds are potent inhibitors of the enzyme activity associated with immunophilin proteins, particularly peptidyl-prolyl isomerase, or rotamase, enzyme activity. A key feature of the neurotrophic compounds is that they do not exert any significant immunosuppressive activity.

Specifically, the present invention relates to a method of effecting a neuronal activity in an animal, comprising:

administering to the animal an effective non-immunosuppressive amount of a compound of formula I:

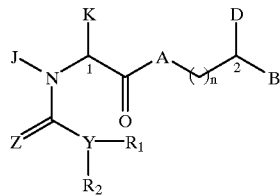

or a pharmaceutically acceptable salt, ester, or solvate thereof, wherein:

A is $CH_2$, O, or NR;

R, B and D are independently Ar, hydrogen, $C_1$–$C_9$ straight or branched chain alkyl, $C_2$–$C_9$ straight or branched chain alkenyl or alkynyl, $C_5$–$C_7$ cycloalkyl substituted $C_1$–$C_9$ straight or branched chain alkyl or $C_2$–$C_9$ straight or branched chain alkenyl or alkynyl, $C_5$–$C_7$ cycloalkenyl substituted $C_1$–$C_9$ straight or branched chain alkyl or $C_2$–$C_9$ straight or branched chain alkenyl or alkynyl, Ar substituted $C_1$–$C_9$ straight or branched chain alkyl, or Ar substituted $C_2$–$C_9$ straight or branched chain alkenyl or alkynyl; wherein any carbon atom of said alkyl is optionally replaced by a heteroatom selected from the group consisting of O, S, SO, $SO_2$ and $NR_3$;

$R_3$ is selected from the group consisting of hydrogen, $C_1$–$C_9$ straight or branched chain alkyl, $C_2$–$C_9$ straight or branched chain alkenyl or alkynyl, and $C_1$–$C_9$ bridging alkyl wherein a bridge is formed between the nitrogen and a carbon atom of said heteroatom-containing chain to form a ring, and wherein said ring is optionally fused to an Ar group;

J is selected from the group consisting of hydrogen, $C_1$–$C_9$ straight or branched chain alkyl, $C_2$–$C_9$ straight or branched chain alkenyl, and —$CH_2Ar$; K is selected from the group consisting of $C_1$–$C_5$ straight or branched chain alkyl, —$CH_2Ar$, and cyclohexylmethyl; or J and K are taken together to form a 5–7 membered heterocyclic ring which is substituted with O, S, SO, or $SO_2$;

Z is O or S;

Y is O or N, provided that
when Y is O, then $R_1$ is a lone pair of electrons and $R_2$ is selected from the group consisting of Ar, $C_1$–$C_9$ straight or branched chain alkyl, and $C_2$–$C_9$ straight or branched chain alkenyl or alkynyl; and
when Y is N, then $R_1$ and $R_2$ are independently selected from the group consisting of Ar, hydrogen, $C_1$–$C_9$ straight or branched chain alkyl, $C_2$–$C_9$ straight or branched chain alkenyl or alkynyl, $C_3$–$C_7$ cycloalkyl, cycloalkenyl or cycloalkynyl, $C_6$–$C_{14}$ bicycloalkyl, bicycloalkenyl or bicycloalkynyl, and $C_9$–$C_{21}$ tricycloalkyl, tricycloalkenyl or tricycloalkynyl; or $R_1$ and $R_2$ are taken together to form a heterocyclic 5–6 membered ring selected from the group consisting of pyrrolidine, imidazolidine, pyrazolidine, piperidine, and piperazine;

Ar is a carbocyclic or heterocyclic aromatic moiety which is unsubstituted or substituted with one or more substituent(s);

q is 0–2; and n is 0 or 1.

The present invention also relates to a method of effecting a neuronal activity in an animal, comprising:
administering to the animal an effective non-immunosuppressive amount of a compound of a compound of formula II or III:

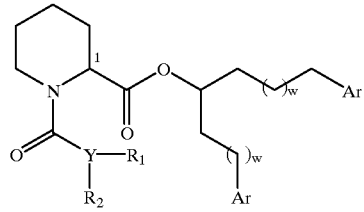

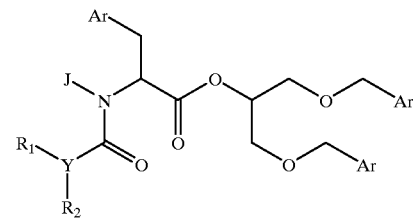

or a pharmaceutically acceptable salt, ester, or solvate thereof, wherein:

Y, $R_1$, $R_2$ and Ar are as defined in the compound of formula I;

J is hydrogen, $C_1$–$C_9$ straight or branched chain alkyl, or $C_2$–$C_9$ straight or branched chain alkenyl; and w is 1 or 2.

The present invention further relates to a method of effecting a neuronal activity in an animal, comprising:
administering to the animal an effective non-immunosuppressive amount of a compound of formula II' or III:

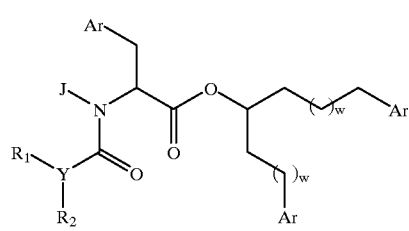

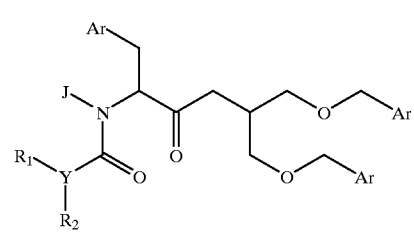

or a pharmaceutically acceptable salt, ester, or solvate thereof, wherein:

Y, $R_1$, $R_2$ and Ar are as defined in the compound of formula I;

J is hydrogen, $C_1$–$C_9$ straight or branched chain alkyl, or $C_2$–$C_9$ straight or branched chain alkenyl; and w is 1 or 2.

Additionally, the present invention relates to a pharmaceutical composition comprising:
(i) an effective non-immunosuppressive amount of a compound of formula I:

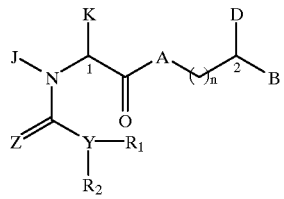

I or a pharmaceutically acceptable salt, ester, or solvate thereof, wherein:

A is $CH_2$, O or NR;

R, B and D are independently Ar, hydrogen, $C_1$–$C_9$ straight or branched chain alkyl, $C_2$–$C_9$ straight or branched chain alkenyl or alkynyl, $C_5$–$C_7$ cycloalkyl substituted $C_1$–$C_9$ straight or branched chain alkyl or $C_2$–$C_9$ straight or branched chain alkenyl or alkynyl, $C_5$–$C_7$ cycloalkenyl substituted $C_1$–$C_9$ straight or branched chain alkyl or $C_2$–$C_9$ straight or branched chain alkenyl or alkynyl, Ar substituted $C_1$–$C_9$ straight or branched chain alkyl, or Ar substituted $C_2$–$C_9$ straight or branched chain alkenyl or alkynyl; wherein any carbon atom of said alkyl is optionally replaced by a heteroatom selected from the group consisting of O, S, SO, $SO_2$ and $NR_3$;

$R_3$ is selected from the group consisting of hydrogen, $C_1$–$C_9$ straight or branched chain alkyl, $C_2$–$C_9$ straight or branched chain alkenyl or alkynyl, and $C_1$–$C_9$ bridging alkyl wherein a bridge is formed between the nitrogen and a carbon atom of said heteroatom-containing chain to form a ring, and wherein said ring is optionally fused to an Ar group;

J is selected from the group consisting of hydrogen, $C_1$–$C_9$ straight or branched chain alkyl, $C_2$–$C_9$ straight or branched chain alkenyl, and —$CH_2Ar$; K is selected from the group consisting of $C_1$–$C_9$ straight or branched chain alkyl, —$CH_2Ar$, and cyclohexylmethyl; or J and K are taken together to form a 5–7 membered heterocyclic ring which is substituted with O, S, SO, or $SO_2$;

Z is O or S;

Y is O or N, provided that when Y is O, then $R_1$ is a lone pair of electrons and $R_2$ is selected from the group consisting of Ar, $C_1$–$C_9$ straight or branched chain alkyl, and $C_2$–$C_9$ straight or branched chain alkenyl or alkynyl; and when Y is N, then $R_1$ and $R_2$ are independently selected from the group consisting of Ar, hydrogen, $C_1$–$C_9$ straight or branched chain alkyl, $C_2$–$C_9$ straight or branched chain alkenyl or alkynyl, $C_3$–$C_7$ cycloalkyl, cycloalkenyl or cycloalkynyl, $C_6$–$C_{14}$ bicycloalkyl, bicycloalkenyl or bicycloalkynyl, and $C_9$–$C_{21}$ tricycloalkyl, tricycloalkenyl or tricycloalkynyl; or $R_1$ and $R_2$ are taken together to form a heterocyclic 5–6 membered ring selected from the group consisting of pyrrolidine, imidazolidine, pyrazolidine, piperidine, and piperazine;

Ar is a carbocyclic or heterocyclic aromatic moiety which is unsubstituted or substituted with one or more substituent(s);

q is 0–2; and n is 0 or 1; and (ii) a pharmaceutically acceptable carrier.

The present invention also relates to a pharmaceutical composition comprising:

(i) an effective non-immunosuppressive amount of a compound of formula II or III for effecting a neuronal activity:

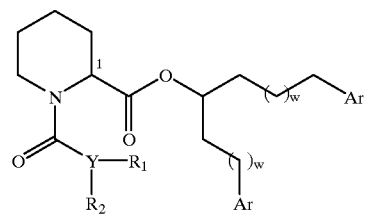

II

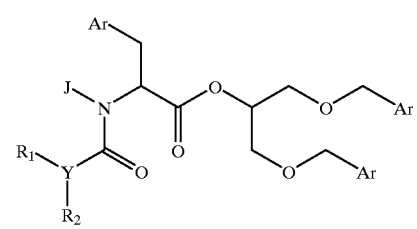

III or a pharmaceutically acceptable salt, ester, or solvate thereof, wherein:

Y, $R_1$, $R_2$ and Ar are as defined in formula I;

J is hydrogen, $C_1$–$C_9$ straight or branched chain alkyl, or $C_2$–$C_9$ straight or branched chain alkenyl; and w is 1 or 2; and (ii) a pharmaceutically acceptable carrier.

The present invention further relates to a pharmaceutical composition comprising:

(i) an effective non-immunosuppressive amount of a compound of formula II' or III for effecting a neuronal activity:

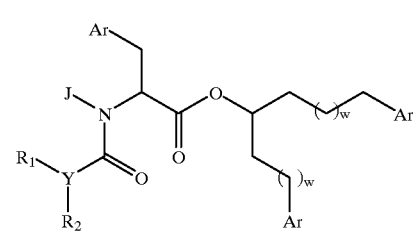

II'

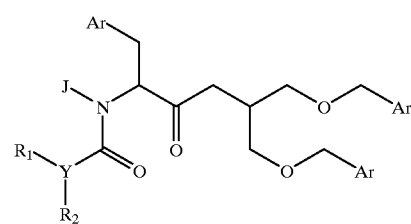

III or a pharmaceutically acceptable salt, ester, or solvate thereof, wherein:

Y, $R_1$, $R_2$ and Ar are as defined in formula I;

J is hydrogen, $C_1$–$C_9$ straight or branched chain alkyl, or $C_2$–$C_9$ straight or branched chain alkenyl; and w is 1 or 2; and (ii) a pharmaceutically acceptable carrier.

The methods and pharmaceutical compositions of the present invention effects neuronal activity and, in particular, promotes nerve growth using only the carbamates and ureas of formulas I, II, II' and III, without any other neurotrophic agents including neurotrophic growth factors.

DETAILED DESCRIPTION OF THE INVENTION

Definitions

"Alkyl" refers to a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Cycloalkyl" refers to a saturated hydrocarbon chain where each carbon atom is linked to two neighboring carbon atoms to form a cyclic structure. Cyclopropyl, cyclobutyl, cyclopentyl, cyclohexyl, cycloheptyl, and cyclooctyl are nonlimiting examples of cycloalkyl derivatives of the present invention. "Bicycloalkyl" refers to cycloalkyl compounds where two or more carbons are shared between two alkyl ring structures. Bicyclopentane, bicyclohexane, bicycloheptane, bicyclooctane, bicyclononane, and bicyclodecane are nonlimiting examples of bicycloalkyl derivatives of the present invention. "Tricycloalkyl" refers to cycloalkyl compounds where two or more carbons are shared between three alkyl ring structures. Adamantyl is a nonlimiting example of tricycloalkyl derivatives of the present invention. The present invention contemplates cyclo-, bicyclo-, and tricycloalkyl compounds which are substituted with the same moieties previously described in the specification as substituents for alkyl groups of the present invention. Bicyclo- and tricycloalkyl compounds are also referred to herein as "fused alkyl ring structures".

"Halo" refers to fluoro, chloro, bromo, or iodo, unless otherwise indicated.

"Isomers" refer to compounds having the same number and kind of atoms, and hence the same molecular weight, but differing in respect to the arrangement or configuration of the atoms. "Stereoisomers" are isomers that differ only in the arrangement of the atoms in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Pharmaceutically acceptable salt" refers to salts of the subject compounds which possess the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

"Treating" refers to:

(i) preventing a disease and/or condition from occurring in a subject which may be predisposed to the disease and/or condition but has not yet been diagnosed as having it;

(ii) inhibiting the disease and/or condition, i.e., arresting its development; and (iii) relieving the disease and/or condition, i.e., causing regression of the disease and/or condition.

Methods of the Invention

The inventors have discovered that certain low molecular weight, small molecule carbamates and ureas have an affinity for FKBP-type immunophilins, particularly FKBP12. When the carbamates and ureas are bound to an FKBP-type immunophilin, they have been found to inhibit the prolyl-peptidyl cis-trans isomerase activity, or rotamase, activity of the binding protein. Unexpectedly, it has been discovered that these non-immunosuppressant compounds also stimulate neurite growth. This activity is useful in the stimulation of is damaged neurons, the promotion of neuronal regeneration, the prevention of neurodegeneration, and the treatment of several neurological disorders known to be associated with neuronal degeneration and peripheral neuropathies.

For the foregoing reasons, the present invention relates to a method of effecting a neuronal activity in an animal, comprising:

administering to the animal an effective non-immunosuppressive amount of a compound of formula I:

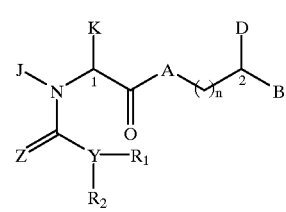

I or a pharmaceutically acceptable salt, ester, or solvate thereof, wherein:

A is $CH_2$, O, or NR;

R, B and D are independently Ar, hydrogen, $C_1$–$C_9$ straight or branched chain alkyl, $C_2$–$C_9$ straight or branched chain alkenyl or alkynyl, $C_5$–$C_7$ cycloalkyl substituted $C_1$–$C_9$ straight or branched chain alkyl or $C_2$–$C_9$ straight or branched chain alkenyl or alkynyl, $C_5$–$C_7$ cycloalkenyl substituted $C_1$–$C_9$ straight or branched chain alkyl or $C_2$–$C_9$ straight or branched chain alkenyl or alkynyl, Ar substituted $C_1$–$C_9$ straight or branched chain alkyl, or Ar substituted $C_2$–$C_9$ straight or branched chain alkenyl or alkynyl; wherein any carbon atom of said alkyl is optionally replaced by a heteroatom selected from the group consisting of O, S, SO, $SO_2$ and $NR_3$;

$R_3$ is selected from the group consisting of hydrogen, $C_1$–$C_9$ straight or branched chain alkyl, $C_2$–$C_9$ straight or branched chain alkenyl or alkynyl, and $C_1$–$C_9$ bridging alkyl wherein a bridge is formed between the nitrogen and a carbon atom of said heteroatom-containing chain to form a ring, and wherein said ring is optionally fused to an Ar group;

J is selected from the group consisting of hydrogen, $C_1$–$C_9$ straight or branched chain alkyl, $C_2$–$C_9$ straight or branched chain alkenyl, and —$CH_2Ar$; K is selected from the group consisting of $C_1$–$C_9$ straight or branched chain alkyl, —$CH_2Ar$, and cyclohexylmethyl; or J and K are taken together to form a 5–7 membered heterocyclic ring which is substituted with O, S, SO, or $SO_2$;

Z is O or S;

Y is O or N, provided that
when Y is O, then $R_1$ is a lone pair of electrons and $R_2$ is selected from the group consisting of Ar, $C_1$–$C_9$ straight or branched chain alkyl, and $C_2$–$C_9$ straight or branched chain alkenyl or alkynyl; and when Y is N, then $R_1$ and $R_2$ are independently selected from the group consisting of Ar, hydrogen, $C_1$–$C_9$ straight or branched chain alkyl, $C_2$–$C_9$ straight or branched chain alkenyl or alkynyl, $C_3$–$C_7$ cycloalkyl, cycloalkenyl or cycloalkynyl, $C_6$–$C_{14}$ bicycloalkyl, bicycloalkenyl or bicycloalkynyl, and $C_9$–$C_{21}$ tricycloalkyl, tricycloalkenyl or tricycloalkynyl; or $R_1$ and $R_2$ are taken together to form a heterocyclic 5–6 membered ring selected from the group consisting of pyrrolidine, imidazolidine, pyrazolidine, piperidine, and piperazine;

Ar is a carbocyclic or heterocyclic aromatic moiety which is unsubstituted or substituted with one or more substituent (s);

q is 0–2; and n is 0 or 1.

In a preferred embodiment, J and K are taken together to form a 5–7 membered heterocyclic ring.

In another preferred embodiment, Ar is selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thio-phenyl, 1H-indazolyl, benzimidazolyl, benzthiazolyl, purinyl, 4H-quinolizinyl, quinolinyl, 1,2,3,4-tetrahydroquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl; wherein Ar is unsubstituted or substituted with one or more substituent(s) independently selected from the group consisting of halogen, hydroxy, nitro, —$SO_3H$, trifluoromethyl, trifluoromethoxy, $C_1$–$C_9$ straight or branched chain alkyl, $C_2$–$C_9$ straight or branched chain alkenyl, O-($C_1$–$C_9$ straight or branched chain alkyl), O-($C_2$–$C_9$ straight or branched chain alkenyl), O-benzyl, O-phenyl, 1,2-methylenedioxy, —$NR_4R_5$, carboxyl, N-($C_1$–$C_9$ straight or branched chain alkyl or $C_2$–$C_9$ straight or branched chain alkenyl) carboxamides, N,N-di-($C_1$–$C_9$ straight or branched chain alkyl or $C_2$–$C_9$ straight or branched chain alkenyl) carboxamides, morpholinyl, piperidinyl, O—X, $CH_2$—$(CH_2)_q$—X, O—$(CH_2)_q$—X, $(CH_2)_q$—O—X, and CH=CH—X;

$R_4$ and $R_5$ are independently selected from the group consisting of $C_1$–$C_9$ straight or branched chain alkyl, $C_2$–$C_9$ straight or branched chain alkenyl, hydrogen, and benzyl; or $R_4$ and $R_5$ are taken together to form a 5–6 membered heterocyclic ring; and X is selected from the group consisting of 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, and pyrimidyl.

In a further preferred embodiment, at least one of said B and D is/are independently represented by the formula —$(CH_2)_r$—(X')—$(CH_2)_s$—Ar, wherein:

r is 1–4;

s is 0–1; and each X' is independently selected from the group consisting of $CH_2$, O, S, SO, $SO_2$, and $NR_6$, wherein $R_6$ is selected from the group consisting of hydrogen, $C_1$–$C_9$ straight or branched chain alkyl, $C_2$–$C_9$ straight or branched chain alkenyl or alkynyl, and $C_1$–$C_9$ bridging alkyl wherein a bridge is formed between the nitrogen atom and Ar.

In an additional preferred embodiment, Ar is selected from the group consisting of phenyl, 2-pyridyl, 3-pyridyl, 4-pyridyl, indolyl, isoindolyl, quinolinyl, isoquinolinyl, 1,2,3,4-tetrahydroiso-quinolinyl, and 1,2,3,4-tetrahydroquinolinyl, wherein said Ar is unsubstituted or substituted with one or more substituent(s) independently selected from the group consisting of hydroxy, nitro, trifluoromethyl, $C_1$–$C_9$ straight or branched chain alkyl, O-($C_1$–$C_9$ straight or branched chain alkyl), halogen, $SO_3H$, and $NR_4R_5$; and $R_4$ and $R_5$ are independently selected from the group consisting of $C_1$–$C_9$ straight or branched chain alkyl, $C_2$–$C_9$ straight or branched chain alkenyl, hydrogen, and benzyl; or $R_4$ and $R_5$ are taken together to form a 5–6 membered heterocyclic ring.

In a more preferred embodiment, Y is N; and $R_1$ and $R_2$ are independently selected from the group consisting of hydrogen, $C_3$–$C_7$ cycloalkyl, $C_6$–$C_{14}$ bicycloalkyl, and $C_9$–$C_{21}$ tricycloalkyl.

In the most preferred embodiment, the compound is 3-(3-pyridyl)-1-propyl (2S)-1-[(2-methylbutyl)-carbamoyl]pyrrolidine-2-carboxylate; 3-(3-pyridyl)-1-propyl (2S)-1-[(1',1'-dimethylpropyl)carbamoyl]pyrrolidine-2-carboxylate; 3-(3-pyridyl)-1-propyl (2S)-1-[(cyclohexyl)-thiocarbamoyl]pyrrolidine-2-carboxylate; 3-(3-pyridyl)-1-propyl (2S)-1-[(cyclohexyl)carbamoyl]pyrrolidine-2-carboxylate; or 3-(3-pyridyl)-1-propyl (2S)-1-[(1-adamantyl)-thiocarbamoyl]pyrrolidine-2-carboxylate.

The present invention also relates to a method of effecting a neuronal activity in an animal, comprising:

administering to the animal an effective non-immunosuppressive amount of a compound of a compound of formula II or III:

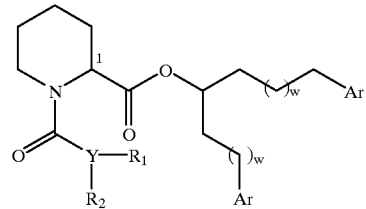

II

-continued

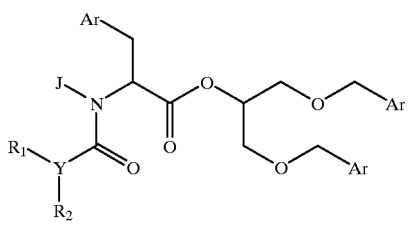
III or a pharmaceutically acceptable salt, ester, or solvate thereof, wherein:

Y, $R_1$, and $R_2$ are as defined in claim 1;

Ar is as defined in claim 8;

J is hydrogen, $C_1$–$C_9$ straight or branched chain alkyl, or $C_2$–$C_9$ straight or branched chain alkenyl; and w is 1 or 2.

The present invention further relates to a method of effecting a neuronal activity in an animal, comprising:

administering to the animal an effective non-immunosuppressive amount of a compound of formula II′ or III:

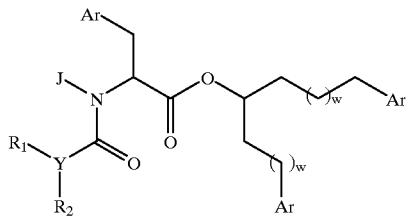
II′

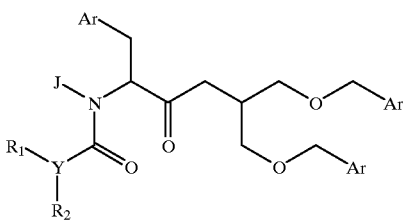
III or a pharmaceutically acceptable salt, ester, or solvate thereof, wherein:

Y, $R_1$, and $R_2$ are as defined in claim 1;

Ar is as defined in claim 8;

J is hydrogen, $C_1$–$C_9$ straight or branched chain alkyl, or $C_2$–$C_9$ straight or branched chain alkenyl; and w is 1 or 2.

The neuronal activity that is effected by the methods of the present invention may be selected from the group consisting of: stimulation of damaged neurons, promotion of neuronal regeneration, prevention of neurodegeneration and treatment of a neurological disorder.

Examples of a neurological disorder that is treatable by the methods of the present invention include without limitation: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; and Parkinson's disease.

The methods of the present invention are particularly useful for treating a neurological disorder selected from the group consisting of: peripheral neuropathy caused by physical injury or disease state, physical damage to the brain, physical damage to the spinal cord, stroke associated with brain damage, and a neurological disorder relating to neurodegeneration. Examples of a neurological disorder relating to neurodegeneration include Alzheimer's Disease, Parkinson's Disease, and amyotrophic lateral sclerosis.

In the methods of the present invention, the neurotrophic compound may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the neurotrophic compounds should readily penetrate the blood-brain barrier when peripherally administered. Compounds which cannot penetrate the blood-brain barrier can be effectively administered by an intraventricular route.

The neurotrophic compounds may also be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, the neurotrophic compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The neurotrophic compounds may further be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

Moreover, the neurotrophic compounds may be administered topically, especially when the conditions addressed for treatment involve areas or organs readily accessible by topical application, including neurological disorders of the eye, the skin, or the lower intestinal tract. Suitable topical formulations can be readily prepared for each of these areas.

For topical application to the eye, or ophthalmic use, the compounds can be formulated as micronized suspensions in isotonic, pH adjusted sterile saline, or, preferably, as a solution in isotonic, pH adjusted sterile saline, either with or without a preservative such as benzylalkonium chloride. Alternatively, the compounds may be formulated into ointments, such as petrolatum, for ophthalmic use.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in a rectal suppository formulations (see above) or in suitable enema formulations.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex, and diet of the patient; the time of administration; the rate of excretion; drug combination; the severity of the particular disease being treated; and the form of administration.

The compounds can be administered alone or with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

Pharmaceutical Compositions of the Invention

Additionally, the present invention relates to a pharmaceutical composition comprising:
(i) an effective non-immunosuppressive amount of a compound of formula I:

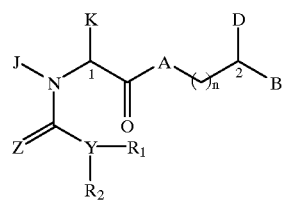

I or a pharmaceutically acceptable salt, ester, or solvate thereof, wherein:
A is $CH_2$, O, or NR;
R, B and D are independently Ar, hydrogen, $C_1$–$C_9$ straight or branched chain alkyl, $C_2$–$C_9$ straight or branched chain alkenyl or alkynyl, $C_5$–$C_7$ cycloalkyl substituted $C_1$–$C_9$ straight or branched chain alkyl or $C_2$–$C_9$ straight or branched chain alkenyl or alkynyl, $C_5$–$C_7$ cycloalkenyl substituted $C_1$–$C_9$ straight or branched chain alkyl or $C_2$–$C_9$ straight or branched chain alkenyl or alkynyl, Ar substituted $C_1$–$C_9$ straight or branched chain alkyl, or Ar substituted $C_2$–$C_9$ straight or branched chain alkenyl or alkynyl; wherein any carbon atom of said alkyl is optionally replaced by a heteroatom selected from the group consisting of O, S, SO, $SO_2$ and $NR_3$;

$R_3$ is selected from the group consisting of hydrogen, $C_1$–$C_9$ straight or branched chain alkyl, $C_2$–$C_9$ straight or branched chain alkenyl or alkynyl, and $C_1$–$C_9$ bridging alkyl wherein a bridge is formed between the nitrogen and a carbon atom of said heteroatom-containing chain to form a ring, and wherein said ring is optionally fused to an Ar group;

J is selected from the group consisting of hydrogen, $C_1$–$C_9$ straight or branched chain alkyl, $C_2$–$C_9$ straight or branched chain alkenyl, and —$CH_2$Ar; K is selected from the group consisting of $C_1$–$C_9$ straight or branched chain alkyl, —$CH_2$Ar, and cyclohexylmethyl; or J and K are taken together to form a 5–7 membered heterocyclic ring which is substituted with O, S, SO, or $SO_2$;

Z is O or S;

Y is O or N, provided that
when Y is O, then $R_1$ is a lone pair of electrons and $R_2$ is selected from the group consisting of Ar, $C_1$–$C_9$ straight or branched chain alkyl, and $C_2$–$C_9$ straight or branched chain alkenyl or alkynyl; and
when Y is N, then $R_1$ and $R_2$ are independently selected from the group consisting of Ar, hydrogen, $C_1$–$C_9$ straight or branched chain alkyl, $C_2$–$C_9$ straight or branched chain alkenyl or alkynyl, $C_3$–$C_7$ cycloalkyl, cycloalkenyl or cycloalkynyl, $C_6$–$C_{14}$ bicycloalkyl, bicycloalkenyl or bicycloalkynyl, and $C_9$–$C_{21}$ tricycloalkyl, tricycloalkenyl or tricycloalkynyl; or $R_1$ and $R_2$ are taken together to form a heterocyclic 5–6 membered ring selected from the group consisting of pyrrolidine, imidazolidine, pyrazolidine, piperidine, and piperazine;

Ar is a carbocyclic or heterocyclic aromatic moiety which is unsubstituted or substituted with one or more substituent(s);

q is 0–2; and n is 0 or 1; and (ii) a pharmaceutically acceptable carrier.

The present invention also relates to a pharmaceutical composition comprising:
(i) an effective non-immunosuppressive amount of a compound of formula II or III for effecting a neuronal activity:

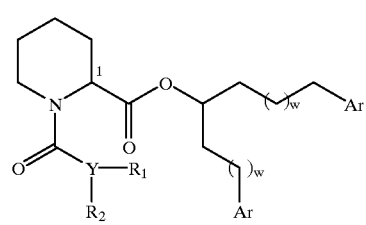

II

-continued

III

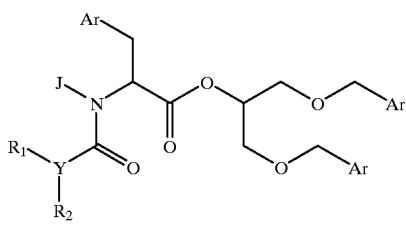

or a pharmaceutically acceptable salt, ester, or solvate thereof, wherein:

Y, $R_1$, and $R_2$ are as defined in claim 21;

Ar is as defined in claim 28;

J is hydrogen, $C_1$–$C_9$ straight or branched chain alkyl, or $C_2$–$C_9$ straight or branched chain alkenyl; and w is 1 or 2; and (ii) a pharmaceutically acceptable carrier.

The present invention further relates a pharmaceutical composition comprising:

(i) an effective non-immunosuppressive amount of a compound of formula II' or III for effecting a neuronal activity:

II'

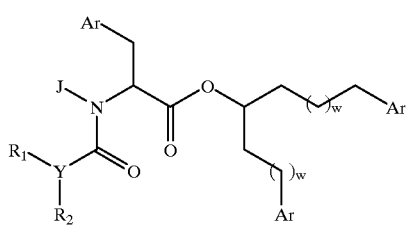

III

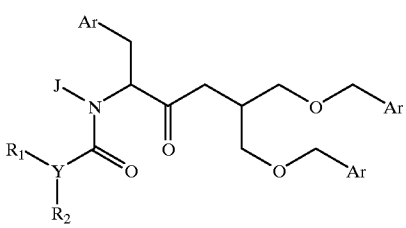

or a pharmaceutically acceptable salt, ester, or solvate thereof, wherein:

Y, $R_1$, and $R_2$ are as defined in claim 21;

Ar is as defined in claim 28;

J is hydrogen, $C_1$–$C_9$ straight or branched chain alkyl, or $C_2$–$C_9$ straight or branched chain alkenyl; and w is 1 or 2; and (ii) a pharmaceutically acceptable carrier.

The preferred neuronal activities and compounds of formulas I, II, II' and III are as described above with regard to the methods of the present invention.

The compounds used in the methods and pharmaceutical compositions of the present invention possess one or more asymmetric center(s) and thus can be produced as mixtures (racemic and non-racemic) of stereoisomers, or as individual R- and S-stereoisomers. The individual stereoisomers may be obtained by using an optically active starting material, by resolving a racemic or non-racemic mixture of an intermediate at some appropriate stage of synthesis, or by resolving a compound of formula I. Unless otherwise indicated, the compounds used in the methods and pharmaceutical compositions of the present invention encompass individual stereoisomers as well as mixtures (racemic and non-racemic) of stereoisomers.

EXAMPLES

The following examples are illustrative of the present invention and are not intended to be limitations thereon. Unless otherwise specified, all percentages are based on 100% by weight of the final compound.

The compounds used in the methods and pharmaceutical compositions of the present invention may be readily prepared by standard techniques of organic chemistry, utilizing the general synthetic pathway depicted below. As described by Scheme I, cyclic amino acids 1 protected by suitable blocking groups P on the amino acid nitrogen may be reacted with alcohols ROH to generate esters 2. After removal of the protecting group, the free amine 3 may be reacted with a variety of isocyanates or isothiocyanates to provide the final ureas or thioureas, respectively. Alternatively, reaction of 1 with amines provides the corresponding amide compounds.

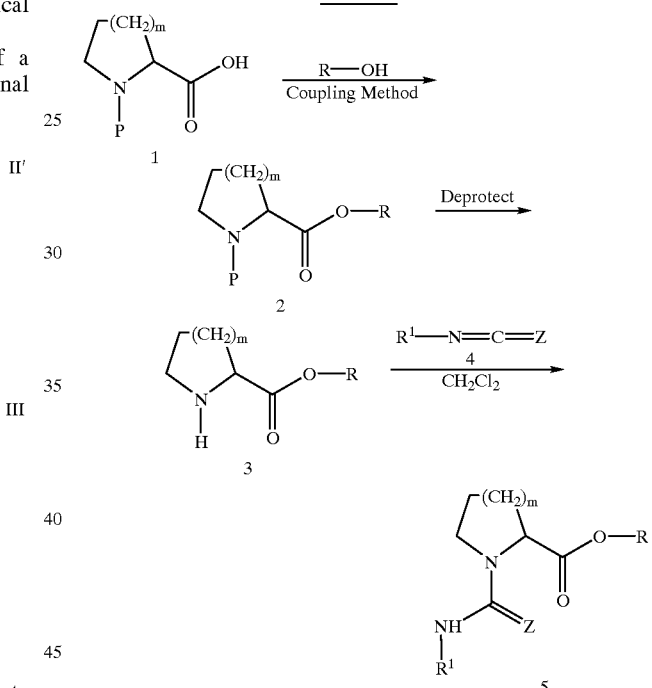

Isocyanates ($R^1NCO$) or isothiocyanates ($R^1NCS$) 4 may be conveniently prepared from the corresponding readily available amines by reaction with phosgene or thiophosgene, as depicted in Scheme II.

Scheme II

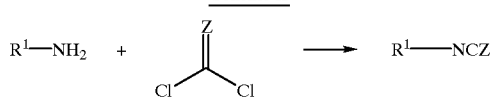

Example 1

Synthesis of 3-(3-pyridyl)-1-propyl (2S)-1-[(2-methylbutyl)carbamoyl]pyrrolidine-2-carboxylate (1)

3-(3-pyridyl)-1-propyl (2S)-N-(tert-butyloxycarbonyl) pyrrolidine-2-carboxylate

A mixture of N-(tert-butyloxycarbonyl)-(S)-proline (3.0 g; 13.9 mmol); 3-(3-Pyridyl)-1-propanol (2.90 g; 20.9 mmol), dicyclohexylcarbodiimide (4.59 g; 22.24 mmol), camphorsulfonic acid (1.08 g; 4.63 mmol), and 4-dimethylaminopyridine (0.60 g; 4.63 mmol) in dry methylene chloride (100 mL) was stirred overnight. The reaction mixture was diluted with methylene chloride (50 mL) and water (100 mL), and the layers were separated. The organic phase was washed with water (3×100 mL), dried over magnesium sulfate, and concentrated, and the crude residue was purified on a silica gel column eluting with ethyl acetate to obtain 4.60 g (95%) of the ester as a thick oil, $^1$H NMR (300 MHz, CDCl$_3$): δ 1.45 (s, 9H); 1.70–2.05 (m, 5H); 2.32 (m, 1H); 2.71 (t, 2H); 3.50 (m, 2H); 4.15 (m, 2H); 4.18 (m, 1H); 7.24 (m, 1H); 7.51 (m, 1H); 8.48 (m, 2H).

3-(3-pyridyl)-1-propyl pyrrolidine-2-carboxylate

A solution of 3-(3-pyridyl)-1-propyl (2S)-N-(tert-butyloxycarbonyl)pyrrolidine- 2-carboxylate (3.00 g; 9 mmol) in methylene chloride (50 mL) and trifluoroacetic acid (5 mL) was stirred at room temperature for three hours. Saturated potassium carbonate was added until the pH was basic, and the reaction mixture was extracted with methylene chloride (3×). The combined organic extracts were dried and concentrated to yield 2.00 g (95%) of the free amine as a thick oil, $^1$H NMR (300 MHz, CDCl$_3$): δ 1.87–2.20 (m, 6H); 2.79 (m, 2H); 3.03 (m, 2H total); 3.07 (m, 2H); 3.84 (m, 1H); 4.24 (m, 2H); 7.32 (m, 1H); 7.60 (m, 1H); 8.57 (m, 2H).

3-(3-pyridyl)-1-propyl (2S)-1-[(2-methylbutyl)-carbamoyl] pyrrolidine-2-carboxylate (1)

A solution of 2-methylbutylamine (113 mg; 1.3 mmol) and triethylamine (132 mg; 1.3 mmol) in methylene chloride (5 mL) was added to a solution of triphosgene (128 mg; 0.43 mmol) in methylene chloride (5 mL). The resulting mixture was refluxed for 1 hour and then cooled to room temperature. 3-(3-Pyridyl)-1-propyl (2S)-pyrrolidine-2-carboxylate (300 mg; 1.3 mmol) in 5 mL of methylene chloride was added and the resulting mixture was stirred for 1 hour and then partitioned between water and a 1:1 mixture of ethyl acetate and hexane. The organic phase was dried, concentrated and purified by column chromatography (50% ethyl acetate/hexane) to obtain 250 mg (55%) of the compound of Example 1 (1, Table I) as an oil, $^1$H NMR (CDCl$_3$, 300 MHz): δ 0.89–0.93 (m, 6H); 1.10–1.20 (m, 1H); 1.27 (s, 1H); 1.36–1.60 (m, 2H); 1.72 (s, 2H); 1.97–2.28 (m, 6H); 2.70–2.75 (m, 2H); 2.92–3.54 (m, 4H); 4.16–4.20 (dt, 2H); 4.45–4.47 (m, 2H); 7.21–7.29 (m, 1H); 7.53–7.56 (dd, 1H); 8.46–8.48 (s, 2H). Anal. Calcd. for C$_{19}$H$_{29}$N$_3$O$_3$—0.5 H$_2$O: C, 64.02; H, 8.48; N, 11.79. Found: C, 63.72; H, 8.42; N, 11.83.

Example 2

Synthesis of 3-(3-pyridyl)-1-propyl (2S)-1-[(1',1'-dimethylpropyl)carbamoyl]pyrrolidine-2-carboxylate (2)

Reaction of 3-(3-pyridyl)-1-propyl (2S) -pyrrolidine-2-carboxylate with the isocyanate generated from tert-amylamine and triphosgene, as described for Example 1, provided the compound of Example 2 (2, Table I) in 62% yield, $^1$H NMR (CDCl$_3$, 300 MHz): δ 0.83 (t, 3H); 1.27 (s, 6H); 1.64–1.71 (m, 2H); 1.91–2.02 (m, 7H); 2.66–2.71 (t, 2H); 3.29–3.42 (m, 2H); 4.11–4.15 (t, 3H); 4.37–4.41 (m, 1H). Anal. Calcd. for C$_{19}$H$_{29}$N$_3$O$_3$—0.5 H$_2$0: C, 64.04; H, 8.48; N, 11.79. Found: C, 64.23; H, 8.31; N, 11.30.

Example 3

Synthesis of 3-(3-pyridyl)-1-propyl (2S)-1-[(cyclohexyl)thiocarbamoyl]-pyrrolidine-2-carboxylate (3)

A mixture of cyclohexylisothiocyanate (120 mg; 0.9 mmol), 3-(3-pyridyl)-1-propyl (2S)-pyrrolidine-2-carboxylate (200 mg; 0.9 mmol) triethylamine (90 mg; 0.9 mmol) in 20 mL of methylene chloride was stirred for 1 hour and then partitioned between water and a 1:1 mixture of ethyl acetate and hexane. The organic phase was dried, concentrated and purified by column chromatography (50% ethyl acetate/hexane) to obtain 160 mg (47%) of the compound of Example 3 (3, Table I), $^1$H NMR (CDCl$_3$, 300 MHz): δ 1.16–1.40 (m, 6H); 1.50–1.71 (m, 4H); 1.95–2.08 (m, 7H); 2.70–2.75 (t, 2H); 3.40–3.60 (m, 2H); 4.17–4.26 (m, 2H); 4.95–4.98 (d, 1H); 5.26–5.29 (d, 1H); 7.17–7.25 (m, 1H). Anal. Calcd. for C$_{20}$H$_{29}$N$_3$O$_2$S: C, 63.97; H, 7.78; N, 11.19. Found: C, 63.25; H, 7.80; N, 11.07.

Example 4

Synthesis of 3-(3-pyridyl)-1-propyl (2S)-1-[(cyclohexyl)carbamoyl]-pyrrolidine-2-carboxylate (4)

A mixture of cyclohexylisocyanate (100 mg; 0.9 mmol), 3-(3-pyridyl)-1-propyl (2S)-pyrrolidine-2-carboxylate (200 mg; 0.9 mmol) and triethylamine (90 mg; 0.9 mmol) in 20 mL of methylene chloride was stirred for 1 hour and then partitioned between water and a 1:1 mixture of ethyl acetate and hexane. The organic phase was dried, concentrated and purified by column chromatography (50% ethyl acetate/ hexane) to obtain 120 mg (36%) of the compound of Example 4 (4, Table I), $^1$H NMR (CDCl$_3$, 300 MHz): δ1.10–1.27 (m, 6H); 1.69–1.75 (m, 4H); 1.94–2.03 (m, 4H); 2.67–2.73 (t, 2H); 3.31–3.44 (m, 3H); 4.12–4.16 (m, 2H); 4.39–4.42 (m, 1H); 7.25–7.34 (m, 1H); 7.25–7.55 (dd, 1H); 8.45 (s, 2H). Anal. Calcd. for C$_{20}$H$_{29}$N$_3$O$_3$—0.6 H$_2$O: C, 64.88; H, 8.22; N, 11.35. Found: C, 64.60; H, 8.18; N, 11.21.

Example 5

Synthesis of 3-(3-pyridyl)-1-propyl (2S)-1-[(1-adamantyl)thiocarbamoyl]pyrrolidine-2-carboxylate (5)

A mixture of 1-adamantylisothiocyanate (250 mg; 0.9 mmol), 3-3-pyridyl)-1-propyl (2S)-pyrrolidine-2-carboxylate (200 mg; 0.9 mmol) and triethylamine (90 mg; 0.9 mmol) in 20 mL of methylene chloride was stirred for 1 hour and then partitioned between water and a 1:1 mixture of ethyl acetate and hexane. The organic phase was dried, concentrated and purified by column chromatography (50% ethyl acetate/hexane) to obtain 150 mg (38%) of the compound of Example 4 (4, Table I), $^1$H NMR (CDCl$_3$, 300 MHz): δ 1.39–1.44 (d, 2H); 1.65 (s, 4H); 1.95–2.07 (m, 8H); 2.07–2.20 (m, 5H); 2.71–2.76 (m, 2H); 3.37–3.45 (m, 1H); 3.50–3.60 (m, 1H); 4.09–4.18 (m, 2H); 4.99–5.21 (d, 1H); 7.21–7.25 (m, 1H). Anal. Calcd. for C$_{24}$H$_{33}$N$_3$O$_2$S—0.4 H$_2$O: C, 66.30; H, 7.84; N, 9.66. Found: C, 66.41; H, 7.79; N, 9.50.

As discussed above, the carbamates and ureas used in the methods and pharmaceutical compositions of the present invention have an affinity for the FK506 binding protein, particularly FKBP12. The inhibition of the prolyl peptidyl cis-trans isomerase activity of FKBP may be measured as an indicator of this affinity.

Ki Test Procedure

Inhibition of the peptidyl-prolyl isomerase (rotamase) activity of the inventive compounds can be evaluated by known methods described in the literature (Harding, et al., *Nature,* 1989, 341:758–760; Holt et al. *J. Am. Chem. Soc.,* 115:9923–9938). These values are obtained as apparent Ki's and are presented in Table II. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent Ki values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

The data for these experiments for representative compounds are presented in Table II under the column "Ki".

The neurotrophic effects of the carbamates and ureas used in the methods and pharmaceutical compositions of the present invention can be demonstrated in cellular biological experiments in vitro, as described below.

Chick Dorsal Root Ganglion Cultures and Neurite Outgrowth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 $\mu$M cytosine $\beta$-D arabinofuranoside (Ara C) at 37° C. in an environment containing 5% $CO_2$. Twenty-four hours later, the DRGs were treated with various immunophilin ligands. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

The data for these experiments for representative compounds are presented in the "ED50" column of Table II.

TABLE I

Examples

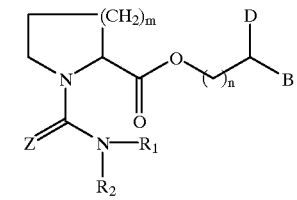

| No. | m | Z | n | D | B | $R_1$ | $R_2$ |
|---|---|---|---|---|---|---|---|
| 1 | 1 | O | 2 | 3-pyridyl | H | 2-methylbutyl | H |
| 2 | 1 | O | 2 | 3-pyridyl | H | 1,1-dimethylpropyl | H |
| 3 | 1 | S | 2 | 3-pyridyl | H | cyclohexyl | H |
| 4 | 1 | O | 2 | 3-pyridyl | H | cyclohexyl | H |
| 5 | 1 | S | 2 | 3-pyridyl | H | 1-adamantyl | H |

TABLE II

In Vitro Activity of Example Compounds

| Example | Ki, nM | ED50, nM |
|---|---|---|
| 1 | 70 | 0.065 |
| 2 | 742 | 1 |
| 3 | 131 | 0.292 |
| 4 | 1482 | n.d. |
| 5 | 116 | 0.141 |

MPTP Model of Parkinson's Disease

The remarkable neurotrophic and neuroregenerative effects of the present inventive compounds were further demonstrated in an animal model of neurodegenerative disease. MPTP lesioning of dopaminergic neurons in mice was used as an animal model of Parkinson's Disease. Four week old male CD1 white mice were dosed i.p. with 30 mg/kg of MPTP for 5 days. Test compounds (4 mg/kg), or vehicle, were administered s.c. along with the MPTP for 5 days, as well as for an additional 5 days following cessation of MPTP treatment. At 18 days following MPTP treatment, the animals were sacrificed and the striata were dissected and perfusion-fixed. Immunostaining was performed on saggital and coronal brain sections using anti-tyrosine hydroxylase 1 g to quantitate survival and recovery of dopaminergic neurons. In animals treated with MPTP and vehicle, a substantial loss of functional dopaminergic terminals was observed as compared to non-lesioned animals. Lesioned animals receiving test compounds showed a significant recovery of TH-stained dopaminergic neurons. Table III presents quantitation for the recovery of TH-positive dopaminergic neurons in the striatum of animals receiving compounds 1, 3, 4 and 5 in this model.

TABLE III

In Vitro Activity of Example Compounds

| Example No. | % Recovery of TH Immunostaining, 4 mg/kg s.c. |
|---|---|
| 1 | 27.47 |
| 2 | n.d. |

TABLE III-continued

In Vitro Activity of Example Compounds

| Example No. | % Recovery of TH Immunostaining, 4 mg/kg s.c. |
|---|---|
| 3 | 56.13 |
| 4 | 59.79 |
| 5 | 52.32 |

All publications and patents identified above are hereby incorporated by reference.

The invention being thus described, it will be obvious that the same may be varied in many ways. Such variations are not to be regarded as a departure from the spirit and scope of the invention and all such modifications are intended to be included within the scope of the following claims.

We claim:

1. A method of effecting a neuronal activity in an animal, comprising:

administering to the animal an effective non-immunosuppressive amount of a compound of formula I:

I or a pharmaceutically acceptable salt, ester, or solvate thereof, wherein:

A is $CH_2$, O, or NR;

R, B and D are independently Ar, hydrogen, $C_1$–$C_9$ straight or branched chain alkyl, $C_2$–$C_9$ straight or branched chain alkenyl or alkynyl, $C_5$–$C_7$ cycloalkyl substituted $C_1$–$C_9$ straight or branched chain alkyl or $C_2$–$C_9$ straight or branched chain alkenyl or alkynyl, $C_5$–$C_7$ cycloalkenyl substituted $C_1$–$C_9$ straight or branched chain alkyl or $C_2$–$C_9$ straight or branched chain alkenyl or alkynyl, Ar substituted $C_1$–$C_9$ straight or branched chain alkyl, or Ar substituted $C_2$–$C_9$ straight or branched chain alkenyl or alkynyl; wherein any carbon atom of said alkyl is optionally replaced by a heteroatom selected from the group consisting of O, S, SO, $SO_2$ and $NR_3$;

$R_3$ is selected from the group consisting of hydrogen, $C_1$–$C_9$ straight or branched chain alkyl, $C_2$–$C_9$ straight or branched chain alkenyl or alkynyl, and $C_1$–$C_9$ bridging alkyl wherein a bridge is formed between the nitrogen and a carbon atom of said heteroatom-containing chain to form a ring, and wherein said ring is optionally fused to an Ar group;

J is selected from the group consisting of hydrogen, $C_1$–$C_9$ straight or branched chain alkyl, $C_2$–$C_9$ straight or branched chain alkenyl, and —$CH_2$Ar; K is selected from the group consisting of $C_1$–$C_9$ straight or branched chain alkyl, —$CH_2$Ar, and cyclohexylmethyl; or J and K are taken together to form a 5–7 membered heterocyclic ring which is substituted with O, S, SO, or $SO_2$;

Z is O or S;

Y is O or N, provided that when Y is O, then $R_1$ is a lone pair of electrons and $R_2$ is selected from the group consisting of Ar, $C_1$–$C_9$ straight or branched chain alkyl, and $C_2$–$C_9$ straight or branched chain alkenyl or alkynyl; and when Y is N, then $R_1$ and $R_2$ are independently selected from the group consisting of Ar, hydrogen, $C_1$–$C_9$ straight or branched chain alkyl, $C_2$–$C_9$ straight or branched chain alkenyl or alkynyl, $C_3$–$C_7$ cycloalkyl, cycloalkenyl or cycloalkynyl, $C_6$–$C_{14}$ bicycloalkyl, bicycloalkenyl or bicycloalkynyl, and $C_9$–$C_{21}$ tricycloalkyl, tricycloalkenyl or tricycloalkynyl; or $R_1$ and $R_2$ are taken together to form a heterocyclic 5–6 membered ring selected from the group consisting of pyrrolidine, imidazolidine, pyrazolidine, piperidine, and piperazine;

Ar is a carbocyclic or heterocyclic aromatic moiety which is unsubstituted or substituted with one or more substituent s);

q is 0–2; and n is 0 or 1.

2. The method of claim 1, wherein the neuronal activity is selected from the group consisting of stimulation of damaged neurons, promotion of neuronal regeneration, prevention of neurodegeneration and treatment of neurological disorder.

3. The method of claim 2, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

4. The method of claim 3, wherein the neurological disorder relating to neurodegeneration is selected from the group consisting of Alzheimer's Disease, Parkinson's Disease, and amyotrophic lateral sclerosis.

5. The method of claim 1, wherein J and K are taken together to form a 5–7 membered ring.

6. The method of claim 1, wherein Ar is selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thio-phenyl, 1H-indazolyl, benzimidazolyl, benzthiazolyl, purinyl, 4H-quinolizinyl, quinolinyl, 1,2,3,4-tetrahydroquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl; wherein Ar is unsubstituted or substituted with one or more substituent(s) independently selected from the group consisting of halogen, hydroxy, nitro, —$SO_3H$, trifluoromethyl, trifluoromethoxy, $C_1$–$C_9$ straight or branched chain alkyl, $C_2$–$C_9$ straight or branched chain alkenyl, O-($C_1$–$C_9$ straight or branched chain alkyl), O-($C_2$–$C_9$ straight or branched chain alkenyl), O-benzyl, O-phenyl, 1,2-methylenedioxy, —$NR_4R_5$, carboxyl, N-($C_1$–$C_9$ straight or branched chain alkyl or $C_2$–$C_9$ straight or branched chain alkenyl) carboxamides, N,N-di-($C_1$–$C_9$ straight or branched chain alkyl or $C_2$–$C_9$ straight or branched chain alkenyl) carboxamides, morpholinyl, piperidinyl, O—X, $CH_2$—$(CH_2)_q$—X, O—$(CH_2)_q$—X, $(CH_2)_q$—O—X, and CH=CH—X;

$R_4$ and $R_5$ are independently selected from the group consisting of $C_1$–$C_9$ straight or branched chain alkyl, $C_2$–$C_9$ straight or branched chain alkenyl, hydrogen, and benzyl; or $R_4$ and $R_5$ are taken together to form a 5–6 membered heterocyclic ring; and X is selected from the group consisting of 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, and pyrimidyl.

7. The method of claim 1, wherein at least one of said B and D is/are independently represented by the formula —$(CH_2)_r$—(X')—$(CH_2)_s$—Ar, wherein:

r is 1–4;

is 0–1; and each X' is independently selected from the group consisting of $CH_2$, O, S, SO, $SO_2$, and $NR_6$, wherein $R_6$ is selected from the group consisting of hydrogen, $C_1$–$C_9$ straight or branched chain alkyl, $C_2$–$C_9$ straight or branched chain alkenyl or alkynyl, and $C_1$–$C_9$ bridging alkyl wherein a bridge is formed between the nitrogen atom and Ar.

8. The method of claim 1, wherein:

Ar is selected from the group consisting of phenyl, 2-pyridyl, 3-pyridyl, 4-pyridyl, indolyl, isoindolyl, quinolinyl, isoquinolinyl, 1,2,3,4-tetrahydroisoquinolinyl, and 1,2,3,4-tetrahydroquinolinyl, wherein said Ar is unsubstituted or substituted with one or more substituent(s) independently selected from the group consisting of hydroxy, nitro, trifluoromethyl, $C_1$–$C_9$ straight or branched chain alkyl, O-($C_1$–$C_9$ straight or branched chain alkyl), halogen, $SO_3H$, and $NR_4R_5$; and $R_4$ and $R_5$ are independently selected from the group consisting of $C_1$–$C_9$ straight or branched chain alkyl, $C_2$–$C_9$ straight or branched chain alkenyl, hydrogen, and benzyl; or $R_4$ and $R_5$ are taken together to form a 5–7 membered heterocyclic ring.

9. The method of claim 1, wherein:

Y is N; and $R_1$ and $R_2$ are independently selected from the group consisting of hydrogen, $C_1$–$C_9$ straight or branched chain alkyl, $C_2$–$C_9$ straight or branched chain alkenyl or alkynyl, $C_3$–$C_7$ cycloalkyl, $C_6$–$C_{14}$ bicycloalkyl, and $C_9$–$C_{21}$ tricycloalkyl.

10. The method of claim 9, wherein the compound is 3-(3-pyridyl)-1-propyl (2S)-1-[(2-methylbutyl)-carbamoyl]pyrrolidine-2-carboxylate.

11. The method of claim 9, wherein the compound is 3-(3-pyridyl)-1-propyl (2S)-1-[(1',1'-dimethylpropyl)-carbamoyl]pyrrolidine-2-carboxylate.

12. The method of claim 9, wherein the compound is 3-(3-pyridyl)-1-propyl (2S)-1-[(cyclohexyl)-thiocarbamoyl]pyrrolidine-2-carboxylate.

13. The method of claim 9, wherein the compound is 3-(3-pyridyl)-1-propyl (2S)-1-[(cyclohexyl)carbamoyl]-pyrrolidine-2-carboxylate.

14. The method of claim 9, wherein the compound is 3-(3-pyridyl)-1-propyl (2S)-1-[(1-adamantyl)-thiocarbamoyl]pyrrolidine-2-carboxylate.

15. A method of effecting a neuronal activity in an animal, comprising:

administering to the animal an effective non-immunosuppressive amount of a compound of a compound of formula II or III:

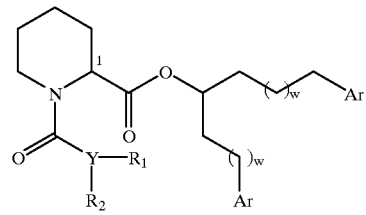

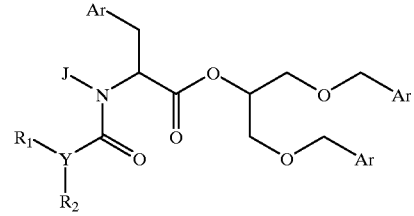

or a pharmaceutically acceptable salt, ester, or solvate thereof, wherein:

Y, $R_1$, and $R_2$ are as defined in claim 1;

Ar is as defined in claim 8;

J is hydrogen, $C_1$–$C_9$ straight or branched chain alkyl, or $C_2$–$C_9$ straight or branched chain alkenyl; and w is 1 or 2.

16. The method of claim 15, wherein the neuronal activity is selected from the group consisting of stimulation of damaged neurons, promotion of neuronal regeneration, prevention of neurodegeneration and treatment of neurological disorder.

17. The method of claim 16, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

18. The method of claim 17, wherein the neurological disorder relating to neurodegeneration is selected from the group consisting of Alzheimer's Disease, Parkinson's Disease, and amyotrophic lateral sclerosis.

19. A method of effecting a neuronal activity in an animal, comprising:

administering to the animal an effective non-immunosuppressive amount of a compound of formula II' or III:

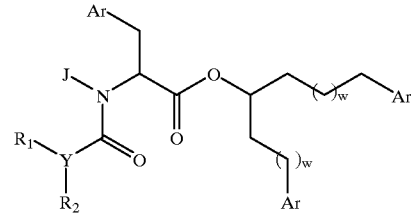

-continued

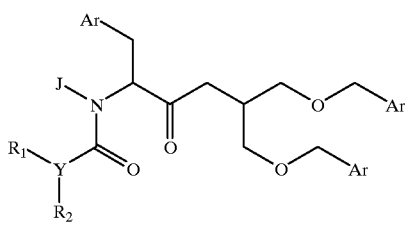

III or a pharmaceutically acceptable salt, ester, or solvate thereof, wherein:
Y, $R_1$, and $R_2$ are as defined in claim 1;
Ar is as defined in claim 8;
J is hydrogen, $C_1$–$C_9$ straight or branched chain alkyl, or $C_2$–$C_9$ straight or branched chain alkenyl; and
w is 1 or 2.

20. The method of claim 19, wherein the neuronal activity is selected from the group consisting of stimulation of damaged neurons, promotion of neuronal regeneration, prevention of neurodegeneration and treatment of neurological disorder.

21. The method of claim 20, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

22. The method of claim 21, wherein the neurological disorder relating to neurodegeneration is selected from the group consisting of Alzheimer's Disease, Parkinson's Disease, and amyotrophic lateral sclerosis.

23. A pharmaceutical composition comprising:
(i) an effective non-immunosuppressive amount of a compound of formula I:

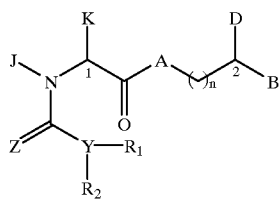

I or a pharmaceutically acceptable salt, ester, or solvate thereof, wherein:
A is $CH_2$, O or NR;
R, B and D are independently Ar, hydrogen, $C_1$–$C_9$ straight or branched chain alkyl, $C_2$–$C_9$ straight or branched chain alkenyl or alkynyl, $C_5$–$C_7$ cycloalkyl substituted $C_1$–$C_9$ straight or branched chain alkyl or $C_2$–$C_9$ straight or branched chain alkenyl or alkynyl, $C_5$–$C_7$ cycloalkenyl substituted $C_1$–$C_9$ straight or branched chain alkyl or $C_2$–$C_9$ straight or branched chain alkenyl or alkynyl, Ar substituted $C_1$–$C_9$ straight or branched chain alkyl, or Ar substituted $C_2$–$C_9$ straight or branched chain alkenyl or alkynyl; wherein any carbon atom of said alkyl is optionally replaced by a heteroatom selected from the group consisting of O, S, SO, $SO_2$ and $NR_3$;
$R_3$ is selected from the group consisting of hydrogen, $C_1$–$C_9$ straight or branched chain alkyl, $C_2$–$C_9$ straight or branched chain alkenyl or alkynyl, and $C_1$–$C_9$ bridging alkyl wherein a bridge is formed between the nitrogen and a carbon atom of said heteroatom-containing chain to form a ring, and wherein said ring is optionally fused to an Ar group;
J is selected from the group consisting of hydrogen, $C_1$–$C_9$ straight or branched chain alkyl, $C_2$–$C_9$ straight or branched chain alkenyl, and —$CH_2$Ar; K is selected from the group consisting of $C_1$–$C_9$ straight or branched chain alkyl, —$CH_2$Ar, and cyclohexylmethyl; or J and K are taken together to form a 5–7 membered heterocyclic ring which is substituted with O, S, SO, or $SO_2$;
Z is O or S;
Y is O or N, provided that
when Y is O, then $R_1$ is a lone pair of electrons and $R_2$ is selected from the group consisting of Ar, $C_1$–$C_9$ straight or branched chain alkyl, and $C_2$–$C_9$ straight or branched chain alkenyl or alkynyl; and
when Y is N, then $R_1$ and $R_2$ are independently selected from the group consisting of Ar, hydrogen, $C_1$–$C_9$ straight or branched chain alkyl, $C_2$–$C_9$ straight or branched chain alkenyl or alkynyl, $C_3$–$C_7$ cycloalkyl, cycloalkenyl or cycloalkynyl, $C_6$–$C_{14}$ bicycloalkyl, bicycloalkenyl or bicycloalkynyl, and $C_9$–$C_{21}$ tricycloalkyl, tricycloalkenyl or tricycloalkynyl; or $R_1$ and $R_2$ are taken together to form a heterocyclic 5–6 membered ring selected from the group consisting of pyrrolidine, imidazolidine, pyrazolidine, piperidine, and piperazine;
Ar is a carbocyclic or heterocyclic aromatic moiety which is unsubstituted or substituted with one or more substituent(s);
q is 0–2; and
n is 0 or 1; and
(ii) a pharmaceutically acceptable carrier.

24. The pharmaceutical composition of claim 23, wherein the neuronal activity is selected from the group consisting of stimulation of damaged neurons, promotion of neuronal regeneration, prevention of neurodegeneration, and treatment of neurological disorder.

25. The pharmaceutical composition of claim 24, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

26. The pharmaceutical composition of claim 25, wherein the neurological disorder relating to neurodegeneration is selected from the group consisting of Alzheimer's Disease, Parkinson's Disease, and amyotrophic lateral sclerosis.

27. The pharmaceutical composition of claim 23, wherein J and K are taken together to form a 5–7 membered ring.

28. The pharmaceutical composition of claim 23, wherein Ar is selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroquinolinyl, isoquinolinyl, 1,2,3,4- tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl; wherein Ar is unsubstituted or substituted with one or more substituent(s) independently selected from the group consisting of halogen, hydroxy, nitro, —SO$_3$H, trifluoromethyl, trifluoromethoxy, C$_1$–C$_9$ straight or branched chain alkyl, C$_2$–C$_9$ straight or branched chain alkenyl, O-(C$_1$–C$_9$ straight or branched chain alkyl), O-(C$_2$–C$_9$ straight or branched chain alkenyl), O-benzyl, O-phenyl, 1,2-methylenedioxy, —NR$_4$R$_5$, carboxyl, N-(C$_1$–C$_9$ straight or branched chain alkyl or C$_2$–C$_9$ straight or branched chain alkenyl) carboxamides, N,N-di-(C$_1$–C$_9$ straight or branched chain alkyl or C$_2$–C$_9$ straight or branched chain alkenyl) carboxamides, morpholinyl, piperidinyl, O—X, CH$_2$—(CH$_2$)$_q$—X, O—(CH$_2$)$_q$—X, (CH$_2$)$_q$—O—X, and CH=CH—X;
  R$_4$ and R$_5$ are independently selected from the group consisting of C$_1$–C$_9$ straight or branched chain alkyl, C$_2$–C$_9$ straight or branched chain alkenyl, hydrogen, and benzyl; or R$_4$ and R$_5$ are taken together to form a 5–6 membered heterocyclic ring; and
  X is selected from the group consisting of 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, and pyrimidyl.
29. The pharmaceutical composition of claim 23, wherein at least one of said B and D is/are independently represented by the formula —(CH$_2$)$_r$—(X')—(CH$_2$)$_s$—Ar, wherein:
  r is 1–4;
  s is 0–1; and
  each X' is independently selected from the group consisting of CH$_2$, O, S, SO, SO$_2$, and NR$_3$, wherein R$_3$ is selected from the group consisting of hydrogen, C$_1$–C$_9$ straight or branched chain alkyl, C$_2$–C$_9$ straight or branched chain alkenyl or alkynyl, and C$_1$–C$_9$ bridging alkyl wherein a bridge is formed between the nitrogen atom and Ar.
30. The pharmaceutical composition of claim 23, wherein:
  Ar is selected from the group consisting of phenyl, 2-pyridyl, 3-pyridyl, 4-pyridyl, indolyl, isoindolyl, quinolinyl, isoquinolinyl, 1,2,3,4-tetrahydroisoquinolinyl, and 1,2,3,4-tetrahydroquinolinyl, wherein said Ar is unsubstituted or substituted with one or more substituent(s) independently selected from the group consisting of hydrogen, hydroxy, nitro, trifluoromethyl, C$_1$–C$_9$ straight or branched chain alkyl, O-(C$_1$–C$_9$ straight or branched chain alkyl), halogen, SO$_3$H, and NR$_3$R$_4$; and
  R$_3$ and R$_4$ are independently selected from the group consisting of C$_1$–C$_9$ straight or branched chain alkyl, C$_2$–C$_9$ straight or branched chain alkenyl, hydrogen, and benzyl; or R$_3$ and R$_4$ are taken together to form a 5–7 membered heterocyclic ring.
31. The pharmaceutical composition of claim 23, wherein:
  Y is N; and
  R$_1$ and R$_2$ are independently selected from the group consisting of hydrogen, C$_3$–C$_7$ cycloalkyl, C$_6$–C$_{14}$ bicycloalkyl, and C$_9$–C$_{21}$ tricycloalkyl.
32. The pharmaceutical composition of claim 31, wherein the compound is 3-(3-pyridyl)-1-propyl (2S)-1-[(2-methylbutyl)-carbamoyl]pyrrolidine-2-carboxylate.
33. The pharmaceutical composition of claim 31, wherein the compound is 3-(3-pyridyl)-1-propyl (2S)-1-[(1',1'-dimethylpropyl)-carbamoyl]pyrrolidine-2-carboxylate.

34. The pharmaceutical composition of claim 31, wherein the compound is 3-(3-pyridyl)-1-propyl (2S)-1-[(cyclohexyl)thiocarbamoyl]pyrrolidine-2-carboxylate.
35. The pharmaceutical composition of claim 31, wherein the compound is 3-(3-pyridyl)-1-propyl (2S)-1-[(cyclohexyl)carbamoyl]pyrrolidine-2-carboxylate.
36. The pharmaceutical composition of claim 31, wherein the compound is 3-(3-pyridyl)-1-propyl (2S)-1-[(1-adamantyl)-thiocarbamoyl]pyrrolidine-2-carboxylate.
37. A pharmaceutical composition comprising:
  (i) an effective non-immunosuppressive amount of a compound of formula II or III for effecting a neuronal activity:

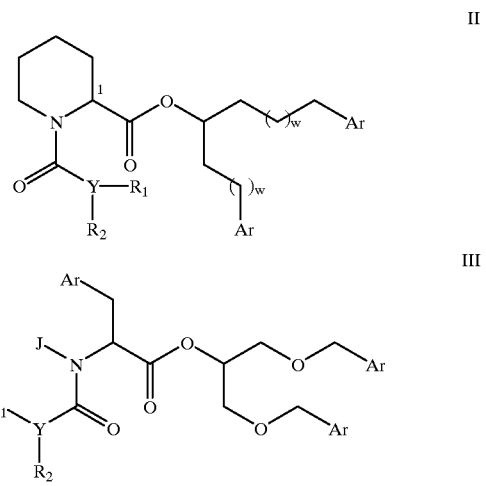

or a pharmaceutically acceptable salt, ester, or solvate thereof, wherein:
  Y, R$_1$, and R$_2$ are as defined in claim 23;
  Ar is as defined in claim 30;
  J is hydrogen, C$_1$–C$_9$ straight or branched chain alkyl, or C$_2$–C$_9$ straight or branched chain alkenyl; and
  w is 1 or 2; and
  (ii) a pharmaceutically acceptable carrier.
38. The pharmaceutical composition of claim 37, wherein the neuronal activity is selected from the group consisting of stimulation of damaged neurons, promotion of neuronal regeneration, prevention of neurodegeneration and treatment of neurological disorder.
39. The pharmaceutical composition of claim 38, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.
40. The pharmaceutical composition of claim 39, wherein the neurological disorder relating to neurodegeneration is selected from the group consisting of Alzheimer's Disease, Parkinson's Disease, and amyotrophic lateral sclerosis.
41. A pharmaceutical composition comprising:
  (i) an effective non-immunosuppressive amount of a compound of formula II' or III for effecting a neuronal activity:

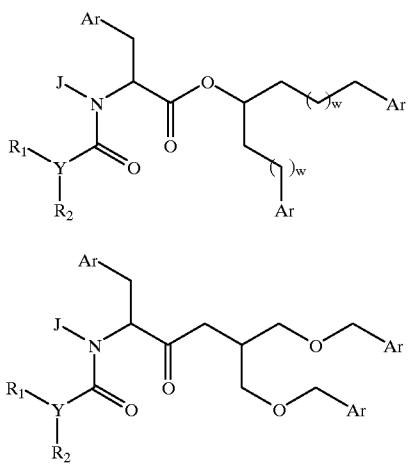

or a pharmaceutically acceptable salt, ester, or solvate thereof, wherein:

Y, $R_1$, and $R_2$ are as defined in claim 23;
Ar is as defined in claim 30;
J is hydrogen, $C_1$–$C_9$ straight or branched chain alkyl, or $C_2$–$C_9$ straight or branched chain alkenyl; and
w is 1 or 2; and
(ii) a pharmaceutically acceptable carrier.

42. The pharmaceutical composition of claim 41, wherein the neuronal activity is selected from the group consisting of stimulation of damaged neurons, promotion of neuronal regeneration, prevention of neurodegeneration and treatment of neurological disorder.

43. The pharmaceutical composition of claim 42, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

44. The pharmaceutical composition of claim 43, wherein the neurological disorder relating to neurodegeneration is selected from the group consisting of Alzheimer's Disease, Parkinson's Disease, and amyotrophic lateral sclerosis.

* * * * *

UNITED STATES PATENT AND TRADEMARK OFFICE
CERTIFICATE OF CORRECTION

PATENT NO. : 6,242,468 B1
DATED : June 5, 2001
INVENTOR(S) : Li, Steiner, Hamilton Page 1 of 1

It is certified that error appears in the above-identified patent and that said Letters Patent is hereby corrected as shown below:

Column 4,
Line 2, after "immunosuppressive amount of a compound" delete "of a compound".

Column 10,
Line 55, after "immunosuppressive amount of a compound" deleste "of a compound".

Column 24,
Line 4-5, after "immunosuppressive amount of a compound" and before "of formula II or III:", delete "of a compound".

Signed and Sealed this

Twentieth Day of November, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.   : 6,242,468 B1
DATED        : June 5, 2001
INVENTOR(S)  : Li, Steiner, Hamilton It is certified that error appears in the above-identified patent and that said Letters Patent is hereby corrected as shown below:

<u>Title page,</u>
"Inventors", after "Jia-He Li, 27" and before "Manor Ct., Cockeysville," please insert the word -- Warren --.

<u>Column 8,</u>
Line 27, after "of" and before "damaged neurons, the promotion of neuronal", please delete the word "is".

<u>Column 10,</u>
Line 46, please delete "(1', 1' - dimethylpropyl) carbamoyl]pyrrolidine-2-"
and replace it with -- (1', 1'-dimethylpropyl) carbomoyl]-pyrrolidine-2- --.
Line 49, after "propel" please delete "(2S)-1-[(cyclohexyl) carbamoyl] pyrrolidine-2-"
and replace it with -- (2S) -1- [ (cyclohexyl) carbamoyl]-pyrrolidine-2- --.

<u>Column 20,</u>
Line 26, before "    Ki,nM    ED50, nM" replace "Example" with -- Example No. --.
Line 61, after "In" and before "Activity of Example Compounds" please delete the word "Vitro" and replace it with -- Vivo --.

<u>Column 23,</u>
Line 19, before "is 0-1;" insert -- s --.

Signed and Sealed this

Nineteenth Day of March, 2002

*Attest:*

JAMES E. ROGAN
*Director of the United States Patent and Trademark Office*

*Attesting Officer*